United States Patent [19]

Christoudias

[11] Patent Number: 5,188,630
[45] Date of Patent: Feb. 23, 1993

[54] CHRISTOUDIAS ENDOSPONGESTICK PROBE

[76] Inventor: George C. Christoudias, 331 River Rd., New Milford, N.J. 07649

[21] Appl. No.: 674,470

[22] Filed: Mar. 25, 1991

[51] Int. Cl.$^5$ .............................................. A61M 29/00
[52] U.S. Cl. ...................... 606/1; 606/191; 604/1; 604/11; 604/96; 604/104
[58] Field of Search ............ 606/108, 1, 191–200; 604/1, 11, 96, 104, 358, 264, 265, 171, 158

[56] References Cited

U.S. PATENT DOCUMENTS

| | | | |
|---|---|---|---|
| 1,909,967 | 5/1933 | Jones | 604/1 |
| 3,882,852 | 5/1975 | Sinnreich | 606/192 |
| 3,978,863 | 9/1976 | Fettel et al. | 606/194 |
| 3,996,938 | 12/1976 | Clark, III | 606/192 |
| 4,198,981 | 4/1980 | Sinnreich | 606/193 |
| 4,921,484 | 5/1990 | Hillstead | 606/194 |
| 4,969,890 | 11/1990 | Sugita | 606/192 |
| 4,993,412 | 2/1991 | Murphy-Chutorian | 606/194 |
| 5,002,556 | 3/1991 | Ishida et al. | 606/192 |
| 5,030,227 | 7/1991 | Rosenbluth et al. | 604/104 |
| 5,074,840 | 12/1991 | Yoon | 604/11 |

FOREIGN PATENT DOCUMENTS

| | | | |
|---|---|---|---|
| 2006019 | 5/1979 | United Kingdom | 606/192 |
| 8606611 | 11/1986 | World Int. Prop. O. | 606/192 |

*Primary Examiner*—Stephen C. Pellegrino
*Assistant Examiner*—Glenn Dawson
*Attorney, Agent, or Firm*—Richard A. Joel

[57] ABSTRACT

A spongestick for endoscopic procedures including a hollow stem of substantially cylindrical cross-section with a longitudinal groove along its outer surface and having a handle at one end and a balloon receptor portion at the other end. The stem is surrounded by a retractable sheath having a handle at the end adjacent the stem handle. A balloon system is included having a Leur lock tip at its upper end for coupling to inflation means and an elongated tube portion which extends within the longitudinal groove in the stem to a tubular balloon which fits over the receptor portion. Circumferential grooves are provided on the upper and lower sections of the receptor portion to accommodate rubber bands which secure a tubular gauze member over the balloon. The gauze member is expanded by inflation of the balloon. The hollow interior of the stem provides a passage for endoscopic instruments such as forceps, dissectors, etc.

8 Claims, 3 Drawing Sheets

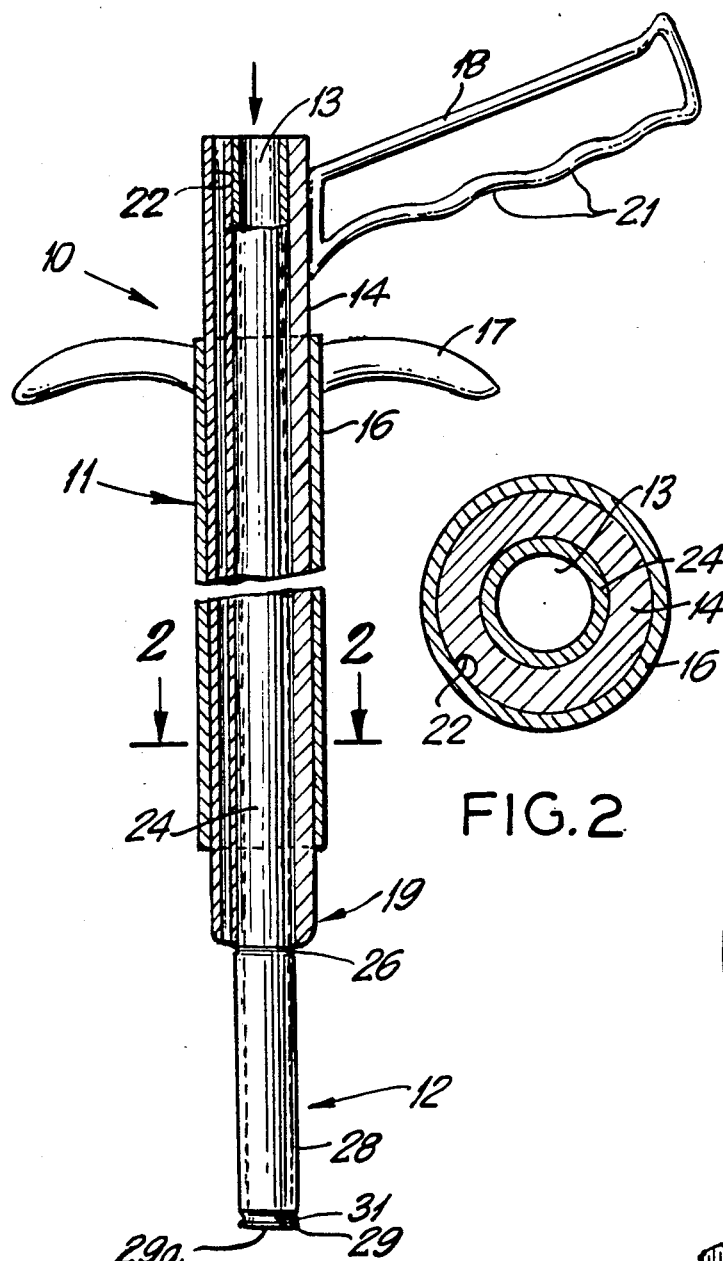
FIG. 1
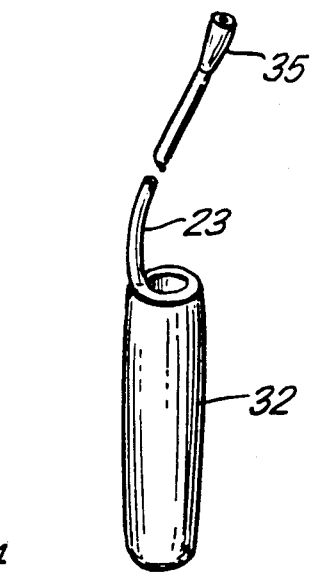
FIG. 3
FIG. 2
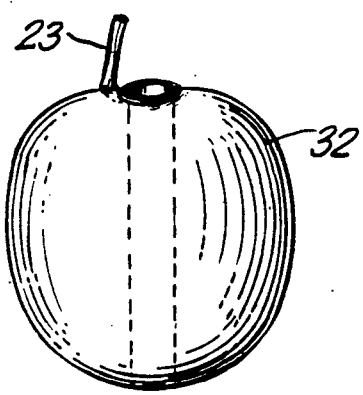
FIG. 4
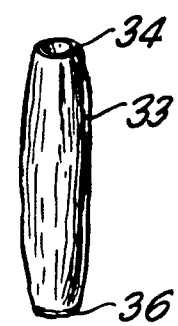
FIG. 5
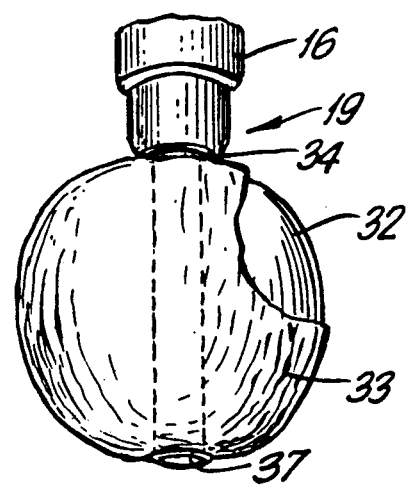
FIG. 6

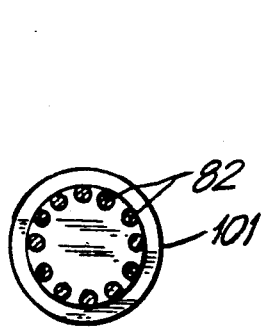
FIG.15
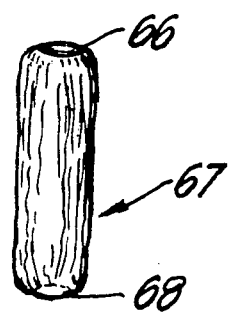
FIG.9
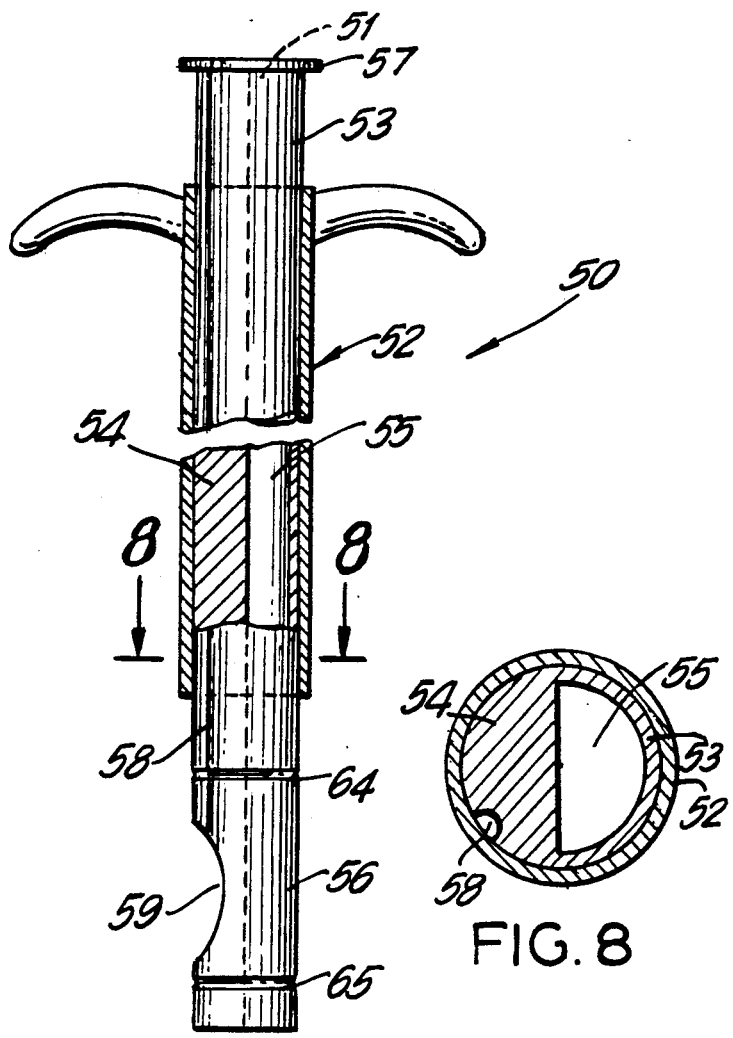
FIG.7
FIG.8
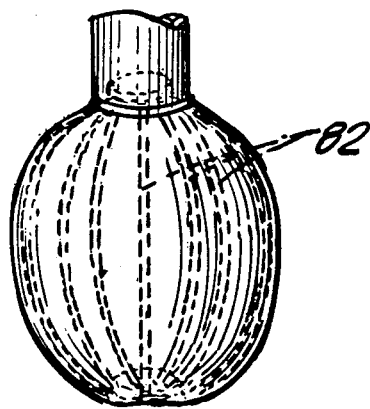
FIG.16
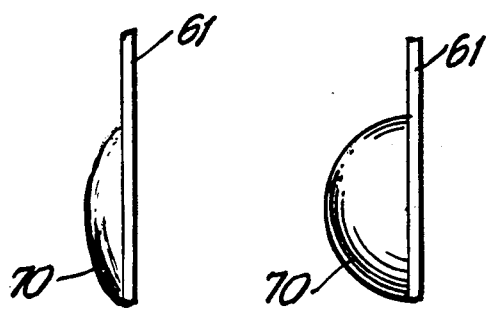
FIG.10a  FIG.10b U.S. Patent    Feb. 23, 1993    Sheet 3 of 3    5,188,630

CHRISTOUDIAS ENDOSPONGESTICK PROBE

BACKGROUND OF THE INVENTION

The endospongestick probe of the present invention is an instrument designed to assist in probing, retracting or sponging intraabdominal viscera or tissue in the performance of laparoscopic surgical procedures.

With endoscopic surgery gaining widespread acceptance in the gynecological and other surgical fields, more and more procedures that were performed with conventional large, painful and temporarily disabling incisions are now utilizing the revolutionary laparoscopic modality. The need for new instruments to perform these procedures is great and the lack of such instruments is a limiting factor in the changeover to endoscopic surgical procedures.

The present invention discloses a basic assembly to facilitate endoscopic surgery. The new instrument is nowhere disclosed in the known prior art. Indeed, the prior art, because of conventional surgical techniques, had little or no use for the invention disclosed herein which is widely useful in an entirely new and revolutionary surgical technique.

SUMMARY OF THE INVENTION

The present invention comprises a spongestick for endoscopic procedures comprising a hollow cylindrical stem with a handle at one end and a balloon receptor at the other end. The stem is surrounded by a retractable sheath having a handle projecting outwardly from its upper end. A balloon system comprising a tubular balloon surrounded by a gauze member is mounted over the receptor. Inflation means are provided to expand the balloon as desired. The hollow interior of the stem provides a passage for endoscopic instruments which function in conjunction with the balloon.

An alternate embodiment of the invention provides a gauze covered balloon which projects outwardly from the side of a half-hollow stem. The stem and retractable sheath are otherwise similar to that previously described.

A further embodiment of the invention provides spring wire means for inflating the balloon which is mounted about a receptor on the stem.

Accordingly, an object of this invention is to provide a new and improved spongestick for endoscopic procedures.

Another object of this invention is to provide a new and improved spongestick for endoscopic procedures which may be used in conjunction with other instruments.

A further object of this invention is to provide a new and improved spongestick for endoscopic procedures which includes an inflatable gauze covered balloon at its lower end, A more specific object of this invention is to provide a new and improved sponge means for endoscopic procedures which includes a stem with a balloon system at its lower end, a handle at its upper end and a retractable sheath surrounding the stem, plus means for inflating and deflating the balloon.

DESCRIPTION OF THE DRAWINGS

The above and other objects of the invention may be more clearly seen when viewed in conjunction with the accompanying drawings wherein:

FIG. 1 is a cross-sectional view of one preferred embodiment of the invention;

FIG. 2 is a view taken along the line 2—2 of FIG. 1;

FIG. 3 is a view of the tubular balloon utilized in connection with the invention of FIG. 1 in an uninflated condition;

FIG. 4 is a view of the balloon in an inflated condition;

FIG. 5 is a view of the tubular gauze member which is mounted over the uninflated balloon;

FIG. 6 is a view of the inflated balloon and gauze cover in place atttached to the endoscopic sponge;

FIG. 7 is a view of an alternate embodiment of the invention;

FIG. 8 is a cross-sectional view taken along the line 8—8 of FIG. 7;

FIG. 9 is a view of the gauze covering for the balloon with the rubber bands at each end;

FIG. 10a is a view of the balloon in a deflated condition and FIG. 10b is a view of the balloon in an inflated condition;

FIG. 15 is a cross-sectional view of the invention taken along the line 15—15 of FIG. 11;

FIG. 16 is a view of the spring wires in a partially expanded condition;

DETAILED DESCRIPTION OF THE INVENTION

Figure 13:
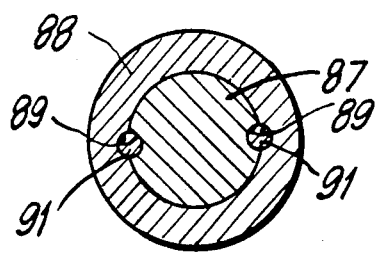
FIG. 13 is a cross-sectional view of the invention taken along the line 13—13 of FIG. 11.

Referring now to the drawings, the invention comprises an endospongestick probe 10 which includes a frame 11 and a balloon system 12. The probe 10 in a preferred embodiment, see FIG. 1, includes an axial aperture 13 for insertion of endoscopic instruments to perform various procedures. The frame comprises a stem 14 consisting of an elongated metal cylinder surrounded by a retractable sheath 16 with outwardly extending handles 17 on either side of the sheath 16.

The frame 11 includes a main cylindrical stem 14, a handle 18 mounted thereto at one end, and a head 19 at the other end containing the balloon system 12. The handle 18 is of surgical steel 2 cm. wide by 3 mm. thick with smooth surfaces. Finger indentations 21 are provided on the lower surface of the handle 18 for gripping purposes. The handle 18 is affixed to the cylinder or stem 14 by conventional means forming an angle of approximately 120 degrees with its stem 14. Manipulation of the handle 18 permits the operator to retract, sponge or probe tissues with the head 19 of the instrument 10.

The main cylindrical stem 14 extends from an open upper end to the head 19. A longitudinal groove 22 extends axially along the surface of the cylinder 14 to accommodate the inlet tube 23 of the balloon system 12. A central tube 24 extends axially within the aperture 13 and projects outwardly from the cylinder 14 including two proximal circumferential grooves 26 about its lower portion projecting from the stem 14. The lower portion of the head 19 comprises a balloon receptor surface 28. The bottom of the tube 24 includes a terminal lip 29 with a circumferential groove 31 thereabout and an exit port 29a for instruments such as a dissector, cautery, laser probe, etc.

FIG. 3 shows the tubular balloon 32 in an uninflated condition while FIG. 4 shows the balloon in an inflated condition. FIG. 5 shows the tubular gauze 33 with proximal and distal rubber bands 34 and 36, respectively, which attach the gauze 33 and balloon 32 in position. The balloon 32 is of various predetermined dimensions with a tubular receptor 28 in its center to provide stability. The balloon 32 is inflated and deflated through the inlet tube 23 with leads to a Leur lock tip 35. Air or sterile non-noxious liquid (e.g., normal saline solution or water) is injected into 35 with a syringe.

In operation, the balloon 32 is inserted over the head (receptor) 28. The tubular gauze 33 is mounted over the balloon 32, with the rubber bands 34 and 36 securing the assembly in place. The balloon 32 is then inflated and the instrument 10 is used as a spongestick. An endoscopic instrument can be inserted through the aperture 13 and out the lower exit port 37 and used while traction or retraction of the adjacent structures is maintained by the spongestick 10.

An alternate embodiment of the invention is shown in FIG. 7. The instrument 50 allows retraction, traction or protection of the tissues while a second instrument such as a dissector, electrocautery or laser probe is being used after accommodation through the hollow compartment 51. The instrument 50 comprises the retractable sheath 52, the stem 53 and the head portion 56. The retractable sheath 52 is identical in design with the retractable sheath 11 of the endospongestick probe 10 as previously described.

The stem 53 is comprised of two components. A hollow half cylinder 55 which is affixed to a solid half cylinder 54 to form a half hollow half solid cylinder or stem of 6 mm. or more in diameter and 0.5 mm. less than the diameter of the sheath. The length of the stem 53 is from 15 to 35 cm. and is between 2 and 6 cm. longer than the retractable sheath 52. The thickness of the wall of the hollow component is 0.2-2 mm. thick.

The free end of the stem 53 is encircled by the sheath stop 57 which is a ring affixed circumferentially at the free end of the stem 53. It is 2 mm. thick and its diameter is equal to that of the stem 53. Running parallel to the main axis of the stem and on the surface of the solid component 54 is a cylindrical groove 58, 1-2.5 mm. in diameter that continues onto the head 56 to the opening 59 of the head. This groove 58 will accommodate the inlet tube 61 of the balloon catheter.

The head 56 includes the hollow 55 and solid 54 components affixed together into a cylindrical structure as in the stem 53. The head 56 varies in length from 3-8 cm. and has on the solid component a symmetrical spherical or eliptical depression 59 starting 1 cm. from the end of the instrument 50 and 5 mm. from the proximal rubber acceptor groove 64. This depression 59 reaches a depth of 1 or more mm. from the main axis of the instrument 50 and accommodates the balloon.

Circumferentially and at a distance of 0.5-1 cm. from the edge of the depression 59 and perpendicular to the main axis lie the proximal groove 64 and distal groove 65 which will accommodate the rubber bands 66 and 68 of the gauze member 67 respectively.

The balloon system is identical to that of the instrument 10 described earlier with the only difference that the balloon 70 expands towards one side of the catheter when insufflated. The gauze 67 is also similar to that previously described and is open at both ends and there is an elastic band 66, 68 at each end.

With the balloon in place, in the receptor recession 59 of the head 56 and the tubular gauze 67 in place about the balloon 70 and the retractable sheath 52 drawn over the head 56, the instrument 50 is inserted through the appropriate trocar port into the abdominal cavity. The sheath 52 is retracted and the balloon insufflated with air or sterile or non-pyrogenic non-toxic fluid (e.g., normal saline or water). The desired operating instrument is inserted via the hollow component into peritoneal cavity through a valve cap which is affixed at the exposed open end to avoid loss of the pneumoperitoneum.

Any instrument such as a tissue dissector, electrocautery or laser probe can be inserted in this fashion into the peritoneal cavity. The adjacent tissues or organs (e.g., liner in cholecystectomy or bowel or abdominal wall in bowel resection to the intended surgical target (gallbladder adhesions, etc.) are retracted with the balloon portion of the instrument 50 the appropriate instrument advanced to the intended target and dissection, resection, cauterization or separation of the target is accomplished by the operator.

The advantages of the balloon retraction are a) tissues are stretched and can be dissected or resected or separated easier; b) normal tissues adjacent to the intended target are retracted away from it and thus protected from the laser probe or electrocautery; and c) by retracting back the operating instrument, the balloon can be used for sponging or probing the different tissues or organs allowing better visualization and exposure of the pathology and/or intended target.

Figure 11:
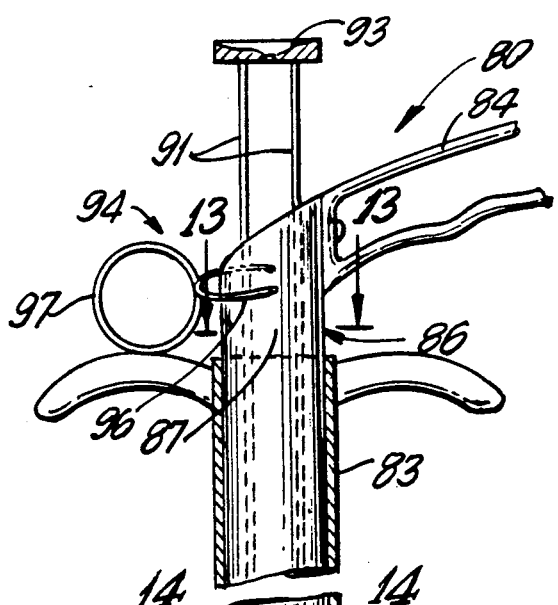
FIG. 11 is a cross-sectional view of an alternate embodiment of the invention.
Figure 18:
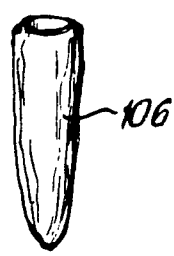
FIG. 18 is a view of the gauze balloon covering.
Figure 14:
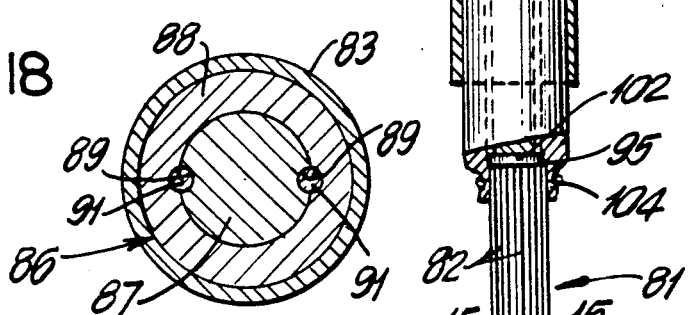
FIG. 14 is a cross-sectional view of the invention taken along the line 14—14 of FIG. 11.
Figure 17:
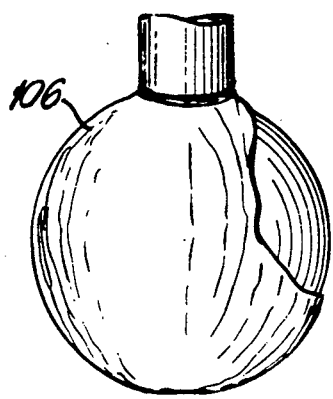
FIG. 17 is a view of the balloon and gauze covering in an expanded condition.
Figure 12:
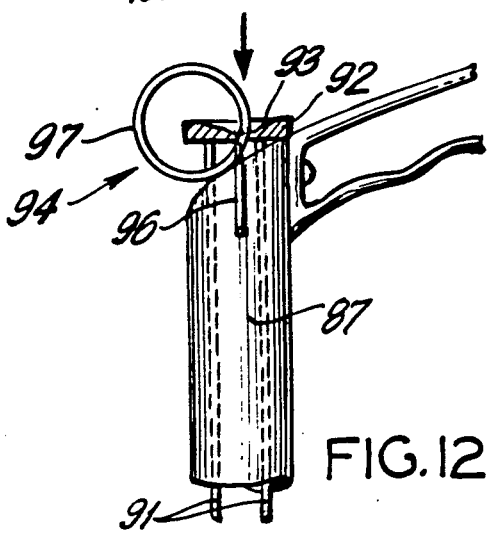
FIG. 12 is a partial view of the handle portion of the invention.

The probe 80 is shown in FIG. 11 as an alternate embodiment of the invention and is similar to the probe 10 of FIG. 1. The fundamental difference is that the expansion of the head 81 is accomplished by pressure on a system of spring ribbons or wires 82 that are compressed between a fixed and a movable point.

This instrument 80 is comprised of retractable sheath 83 identical to the retractable sheath 16 of probe 10, and a solid frame comprising the handle 84, the stem 86 and the head 81.

The handle 84 is identical with the handle of the probe 10 and the stem 86 of probe 80 is similar in dimensions to the stem 14 of probe 10 with the following differences in its features. The stem 86 has no groove along its surface. The stem 86 has two components—a central cylindrical, solid structure 87 of 3-5 mm. in diameter and a peripheral cylindrical tubular structure 88 of 2-9 mm. in diameter and 2-7 mm. in wall thickness. The central structure 87 fits into the peripheral structure 88 and both are slidably mounted together to form the stem 86. Diametrically opposite and on the inner surface of the peripheral tubular surface 88 and the convex surface of the central solid cylinder 87 are two semicircular 0.5 mm. to 2 mm. wide grooves 89 that run parallel to the long axis of the stem 86. When assembled, these two components of the stem 86 are fixed in position with each groove 89 of each instrument facing perfectly the groove of the other instrument so that a cylindrical path is created which will accommodate the control wires 91. The wall of the tubular peripheral structure 88 at the distal 1.5 cm. towards the head is thinner by 1 mm. than the rest of the proximal peripheral structure the difference being carved out of the inside surface of the structure so that a circular space of 1 mm. is created to accommodate the pressure ring 95 and spring ribbons or wires 82.

Within the cylindrical path between the peripheral 88 and central 87 structures are located the control wires 91 which are between 0.5 mm. and 2 mm. in diameter. These control wires 91 project 2 cm. to 4 cm. beyond the stem 86 at the handle end of the stem 86 and converge to a 2 mm. ring 92 which encircles the (central) main axis of the stem 86. Onto this ring 92 concave handle 93 is affixed at its center where the two limbs lead into a 5 mm. depression 1.5 mm. deep and 5 mm. wide, in the center of which there is a 2 mm. ring 92 for affixing this handle 84 onto the ring 92 of the control wires 91. This depression will accommodate the swing spring 94 and keep the head expansion in place after advancement of the control wires 91 towards the head 81.

On the handle side of the stem 86 at diametrically opposite sides and at right angles to the plane between the control wires 91 is affixed a swing loop spring 96 at 2 points 1.5 cm. from the points of exit of the control wires 91 from the stem 86. This loop swing spring 96 is 2 cm. long and through its loop passes a 2 cm. control ring 97 which with the appropriate traction arms the ring 97 and positions it over the depression (5a) of handle 84 of the activated control wires 91, thus securing the activated control wires 91 in place and maintaining the expansion of the head 81.

The head 81 is comprised of a central solid cylinder 98 which is a continuation of the upper solid central cylinder portion of the stem 86 and is of a diameter of 1-3 mm. less than the diameter of the stem central cylinder 98. This cylinder 87 is 2-6 cm. long and at its tip is attached at the center of the concave surface of a thick cup 99, thus forming a stop to the distal ring 101.

Over this central cylinder 98 and affixed on two rings 101, 102 are between one and 20 spring ribbons and/or spring wires 82 which when compressed between the proximal 102 and distal rings 101, by advancement of the control wires 91 mushroom out into a spherical structure that will expand the diameter of the head 81. The rubber band receptor groove 104 is identical to that of probe 10. The tubular gauze 106 is identical to the tubular gauze described with regard to probe 10 except that endoscopic instruments can be inserted through gauze member 36.

In use the tubular gauze 106 is placed over the wires 82 in the head 81 with the rubber band resting in the respective groove 104. The retractable sheath 83 is advanced over the head 81 and the instrument inserted via the trocar port into the abdominal cavity. The sheath 83 is retracted towards the handle 84 and the control wires 91 advanced and secured in place with the loop swing spring. The probe 80 is then ready to be used.

While the invention has been explained by a detailed description of certain specific embodiments, it is understood that various modifications and substitutions can be made in any of them within the scope of the appended claims which are intended also to include equivalents of such embodiments.

What is claimed is:

1. A spongestick for endoscopic procedures used in conjunction with endoscopic instruments comprising:
    a main rigid stem comprising an elongated cylinder having an axial aperture extending therethrough, an outer cylinder surface having a longitudinal groove extending along said outer surface, an upper cylinder portion having a handle projecting outwardly from said upper portion and a lower cylinder portion;
    a retractable cylindrical sheath slidably mounted about the stem cylinder having an upper portion and at least one handle extending outwardly from the upper portion thereof;
    a central tube for insertion of endoscopic instruments therethrough mounted within the stem aperture and extending outwardly therefrom, said tube including an upper circumferential groove adjacent the stem and a lower tube portion having a lower circumferential groove; and
    a balloon and a tubular gauze member surrounding the balloon at the lower portion of the central tube and having upper and lower elastic bands which mount in the respective circumferential tube grooves securing said balloon and gauze member in position, said balloon having an elongated inflation tube extending upwardly along the longitudinal groove to the upper portion of the stem cylinder, and wherein the balloon and gauze member include axial apertures through which the tube extends.

2. A spongestick for endoscopic procedures in accordance with claim 1 wherein:
    the retractable sheath includes two handles, each extending outwardly on opposite sides of the sheath at its upper portion and the balloon inflation tube includes an upper portion having a Leur lock tip mounted thereto.

3. A spongestick for endoscopic procedures used in conjunction with endoscopic instruments comprising:
    a rigid stem comprising an elongated hollow cylinder having upper and lower portions and internal and external cylinder walls for insertion of endoscopic instruments therethrough; said hollow cylinder further comprising a solid portion and a hollow portion extending along the length thereof;
    a retractable rigid sheath slidably mounted about the stem and having at least one handle projecting outwardly therefrom;
    said lower portion having a concave recess within the solid portion of the external cylinder wall;
    balloon means mounted about the lower portion of the stem within said recess; and
    means for inflating said balloon means to protrude outwardly from said recess.

4. A spongestick in accordance with claim 3 and further comprising: a groove extending longitudinally along the external cylinder wall extending from said recess to the upper portion of the stem, and said means for inflating said balloon means including an elongated inflation tube connected to said balloon means and positioned within the longitudinal groove of the stem and extending to the upper portion of the stem, wherein said hollow portion of the stem may be used for endoscopic procedures.

5. A spongestick in accordance with claim 3 wherein:
    said stem further includes a pair of circumferentially spaced grooves about said lower portion of said cylinder, said balloon means comprising a balloon, a flexible gauze cover surrounding the balloon and means for securing ends of said balloon means within said circumferential grooves.

6. A spongestick for endoscopic procedures and used in conjunction with endoscopic instruments comprising:

a main hollow rigid stem comprising a cylinder having upper and lower portions and internal and external cylinder walls, said stem including a handle extending outwardly from said upper portion at an angle thereto and atleast two longitudinal grooves extending longitudinally along the the internal cylinder wall thereof from the upper portion of the cylinder to the lower portion thereof; and further including a solid elongated tube having upper and lower ends mounted within the cylinder and having an external wall and at least two longitudinal grooves extending along the external tube wall opposite the longitudinal cylinder grooves in the internal cylinder wall and forming passageways;

a lower member mounted adjacent the lower end of the tube having resilient means extending downwardly, and a fixed bottom platform, said resilient means connected between said lower member and said platform, and control wires mounted to the lower member and extending upwardly through the groove passageways and having an upper end extending outwardly therefrom; and further comprising balloon means mounted about the resilient means between the lower member and the platform, said balloon means being expanded by activation of said control wires.

7. A spongestick in accordance with claim 6 further including:

a ring mounted to the upper end of the control wires and means on the upper end of the stem cylinder to engage the ring and lock the control wires in position with the balloon means expanded.

8. The method of endoscopically sponging a patient comprising the steps of:

providing an elongated sponging instrument for insertion into a patient, said instrument having an interior stem and an external sheath;

inserting a balloon over the stem of the instrument projecting from the sheath;

mounting a tubular gauze member over the balloon prior to inflation;

sliding the sheath over the gauze member, balloon and interior stem before insertion of the instrument into a body cavity;

inserting the sponging instrument into a body cavity in a patient;

retracting the sheath and inflating the balloon to expand the gauze for contact with the patient within the body cavity, and manipulating the instrument with the handle and sheath to perform a sponging operation.

* * * * *